United States Patent
Yoon et al.

(10) Patent No.: US 10,077,468 B2
(45) Date of Patent: Sep. 18, 2018

(54) PCR PRIMER CAPABLE OF REDUCING NON-SPECIFIC AMPLIFICATION AND PCR METHOD USING THE PCR PRIMER

(75) Inventors: Seongjun Yoon, Seoul (KR); Hyunyoung Lee, Sungnam-Si (KR); Jinseok Yu, Okcheon-Yup (KR); Sooyoun Jun, Seoul (KR); Sanghyeon Kang, Seoul (KR)

(73) Assignee: iNtRON Biotechnology, Inc., Sungnam-Si (KR)

( * ) Notice: Subject to any disclaimer, the term of this patent is extended or adjusted under 35 U.S.C. 154(b) by 1056 days.

(21) Appl. No.: 12/228,302

(22) Filed: Aug. 12, 2008

(65) Prior Publication Data
US 2009/0258353 A1 Oct. 15, 2009

(30) Foreign Application Priority Data
Apr. 15, 2008 (KR) .................. 10-2008-0034797

(51) Int. Cl.
  *C12Q 1/68* (2018.01)
  *C12Q 1/686* (2018.01)
(52) U.S. Cl.
  CPC .................... *C12Q 1/686* (2013.01)
(58) Field of Classification Search
  None
  See application file for complete search history.

(56) References Cited

U.S. PATENT DOCUMENTS 5,866,336 A * 2/1999 Nazarenko et al. .............. 435/6
6,277,607 B1 * 8/2001 Tyagi .................. C12Q 1/6818
                                                          435/5
(Continued)

FOREIGN PATENT DOCUMENTS

JP        200624784    9/2006
KR    10-2005-0028904    3/2005
(Continued)

OTHER PUBLICATIONS

Liu et al. Changes of 5' terminal nucleotides of PCR primers causing variable T-A cloning efficiency. Journal of Integrative Plant Biology 49(3):382-385, Mar. 2007.*
(Continued)

*Primary Examiner* — Samuel C Woolwine
(74) *Attorney, Agent, or Firm* — Ballard Spahr LLP

(57) ABSTRACT

The present invention relates to a PCR primer facilitating hot-start PCR by suppressing non-specific amplification at room temperature and at the same time capable of reducing significantly non-specific amplification by dominating the amplification of the PCR product rather than the amplification of the original template from the third PCR cycle, more precisely a PCR primer prepared by additionally inserting the reverse-complementary sequence to a certain region starting from the 5'-start site of the 5'-terminus of the original primer which is composed of priming sequence to anneal to a PCR template into the 5'-terminus of the original primer and a PCR method using the same. The primer of the present invention has a original primer sequence composed of priming sequence to anneal to a PCR template and an additional reverse-complementary sequence, which inserted into the 5'-terminus of the original primer, to a certain region starting from the 5'-start site of the 5'-terminus of the original primer sequence, suggesting that a template-specific sequence and its reverse-complementary sequence are included in the same primer. The present invention can improve PCR specificity by reducing non-specific amplification.

2 Claims, 10 Drawing Sheets
Specification includes a Sequence Listing.

(56) References Cited

U.S. PATENT DOCUMENTS

2004/0023207 A1* 2/2004 Polansky .................. 435/5
2007/0128620 A1* 6/2007 Lao .................. C12Q 1/6844
                                                          435/6.11

FOREIGN PATENT DOCUMENTS

WO    WO 0173087 A1 * 10/2001  ........... C07K 14/005
WO    WO 2003/050305      6/2003

OTHER PUBLICATIONS

Machine Translation of JP 2006-254784, published Sep. 28, 2006 (14 pages).*
GenBank U93275.1 [online] Oct. 22, 1997 [retrieved on Sep. 6, 2016] retrieved from https://www.ncbi.nlm.nih.gov/nuccore/U93275.1?report=genbank.*
GenBank AF178081.1 [online] Jan. 24, 2000 [retrieved on Sep. 6, 2016] retrieved from http://www.ncbi.nlm.nih.gov/nuccore/AF178081.1?report=genbank.*
GenBank KJ485850.1 [online] Jun. 24, 2014 [retrieved on Sep. 6, 2016] retrieved from http://www.ncbi.nlm.nih.gov/nuccore/kj485850.1.*
D'Aquila RT, Bechtel LJ, Videler JA, Eron JJ, Gorczyca P, Kaplan JC. (1991) Maximizing sensitivity and specificity of PCR by pre-amplification heating. Nucleic Acids Res., 19(13): 3749.
Dang C, Jayasena SD. (1996) Oligonucleotide inhibitors of Taq DNA polymerase facilitate detection of low copy number targets by PCR. J. Mol. Biol., 264(2): 268-278.
Erlich HA, Gelfand D, Sninsky JJ. (1991) Recent advances in the polymerase chain reaction. Science, 252(5013): 1643-1651.
Kaboev OK, Luchkina LA, Tret'iakov AN, Bahrmand AR. (2000) PCR hot start using primers with the structure of molecular beacons (hairpin-like structure). Nucleic Acids Res., 28(21):E94.
Kellogg DE, Rybalkin I, Chen S, Mukhamedova N, Vlasik T, Siebert PD, and Chenchik A. (1994) Taqstart Antibody™: "Hot Start" PCR Facilitated by a Neutralizing Monoclonal Antibody Directed Against Taq DNA Polymerase. BioTechniques, 16(6): 1134-1137.

* cited by examiner

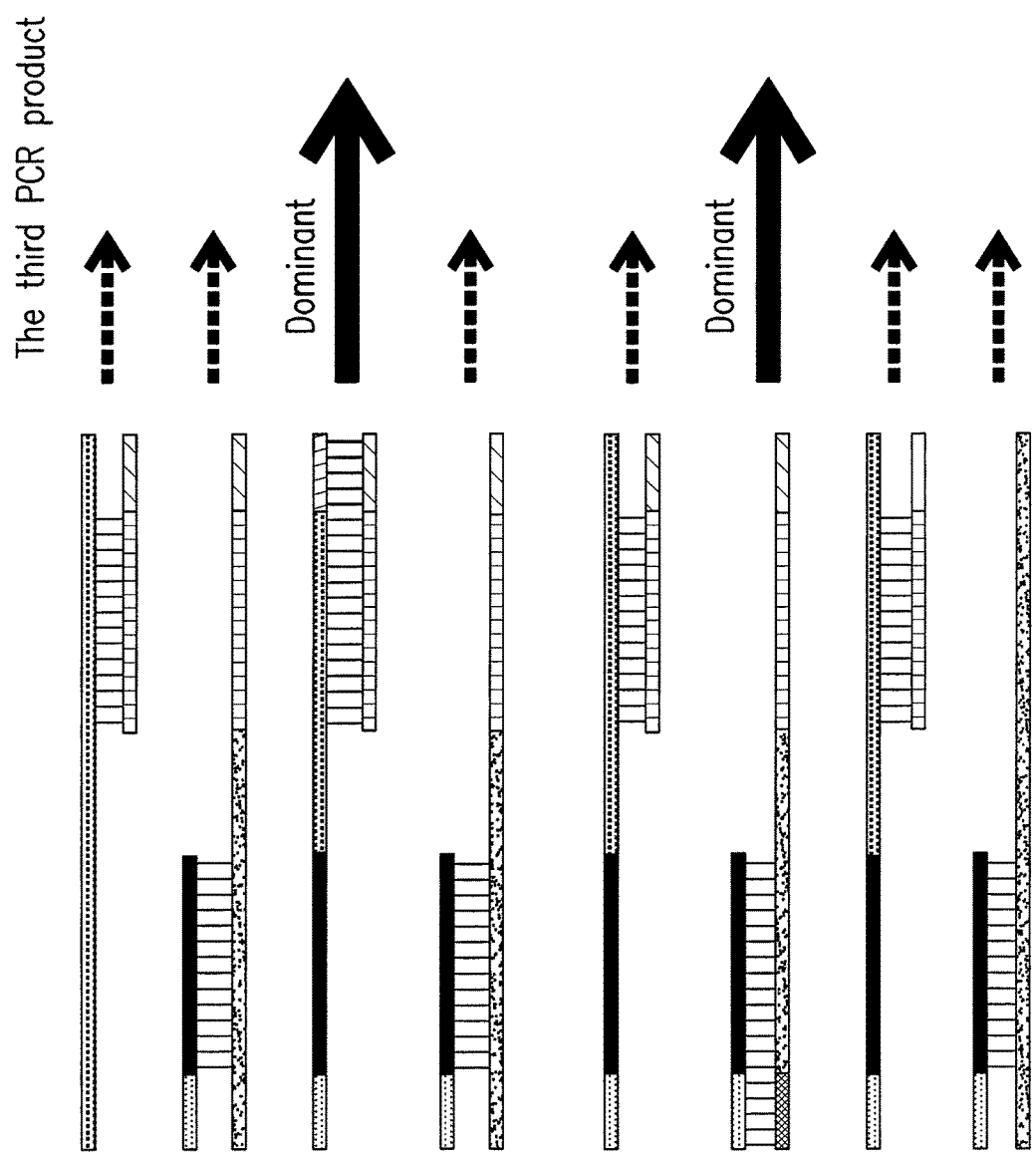

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: first original forward primer

<400> SEQUENCE: 1
cctatcaact ttcgatggta gt                                              22

<210> SEQ ID NO 2
<211> LENGTH: 20
<212> TYPE: DNA
```

```
<213> ORGANISM: Artificial Sequence
<220> FEATURE:
<223> OTHER INFORMATION: first original reverse primer

<400> SEQUENCE: 2
cgctccacca actaagaacg                                            20

<210> SEQ ID NO 3
<211> LENGTH: 28
<212> TYPE: DNA
<213> ORGANISM: Artificial Sequence
<220> FEATURE:
<223> OTHER INFORMATION: first modified forward primer

<400> SEQUENCE: 3
gataggccta tcaactttcg atggtagt                                   28

<210> SEQ ID NO 4
<211> LENGTH: 26
<212> TYPE: DNA
<213> ORGANISM: Artificial Sequence
<220> FEATURE:
<223> OTHER INFORMATION: first modified reverse primer

<400> SEQUENCE: 4
ggagcgcgct ccaccaacta agaacg                                     26

<210> SEQ ID NO 5
<211> LENGTH: 16
<212> TYPE: DNA
<213> ORGANISM: Artificial Sequence
<220> FEATURE:
<223> OTHER INFORMATION: second original forward primer

<400> SEQUENCE: 5
cctatcaact ttcgat                                                16

<210> SEQ ID NO 6
<211> LENGTH: 16
<212> TYPE: DNA
<213> ORGANISM: Artificial Sequence
<220> FEATURE:
<223> OTHER INFORMATION: second original reverse primer

<400> SEQUENCE: 6
cgctccacca actaag                                                16

<210> SEQ ID NO 7
<211> LENGTH: 22
<212> TYPE: DNA
<213> ORGANISM: Artificial Sequence
<220> FEATURE:
<223> OTHER INFORMATION: second modified forward primer

<400> SEQUENCE: 7
gataggccta tcaactttcg at                                         22

<210> SEQ ID NO 8
<211> LENGTH: 22
<212> TYPE: DNA
<213> ORGANISM: Artificial Sequence
<220> FEATURE:
<223> OTHER INFORMATION: second modified reverse primer
```

-continued

```
<400> SEQUENCE: 8
ggagcgcgct ccaccaacta ag                                            22
```

PCR PRIMER CAPABLE OF REDUCING NON-SPECIFIC AMPLIFICATION AND PCR METHOD USING THE PCR PRIMER

CROSS REFERENCE TO RELATED APPLICATION

This application claims priority to Korean Patent Application No. 2008/0034797, filed Apr. 15, 2008, which application is incorporated by this reference in its entirety.

TECHNICAL FIELD

The present invention relates to the design and synthesis of a PCR primer capable of inhibiting or reducing non-specific amplification significantly in PCR. Precisely, the PCR primer is prepared by inserting the reverse-complementary sequence to a certain region starting from the 5'-start site of the 5'-terminus of the original primer which is composed of priming sequence to anneal to a PCR template, additionally into the 5'-terminus of the original primer, by which PCR is suppressed before reaching the proper reaction temperature for PCR (the temperature securing specificity in annealing between a primer and a template which largely depends on Tm of a primer and generally at least 40° C.). In addition, the primer of the present invention is also capable of inhibiting the amplification of the initially added template itself (referred as "original template" in this invention) so as to inhibit or reduce non-specific amplification of PCR. The present invention also relates to a PCR method using the primer.

BACKGROUND ART

PCR is a molecular biological method that is capable of amplifying a target DNA exponentially. Any part of DNA can be amplified once its sequence is identified. PCR was first proposed by K. Mullis in mid-1980s. Since then, PCR has been widely used in biological research fields including molecular genetics which studies genes. PCR exploits the DNA replication activity of DNA polymerase. DNA polymerase facilitates the synthesis of complementary DNA molecule by using single stranded DNA molecule as a template. This single stranded DNA molecule can be obtained simply by boiling a double stranded DNA molecule. This procedure is called 'DNA denaturation'. In order for DNA polymerase to start DNA synthesis, start site has to be double stranded DNA form. So, to form double stranded DNA, small DNA fragments capable of binding complementarily to both ends of a template DNA should be added in PCR. This complementary binding between DNA fragments and a template DNA is annealing. Only after annealing, DNA synthesis by DNA polymerase can be started. The complementary DNA fragments capable of binding to both ends of a target DNA sequence to be amplified are called oligonucleotide primer or simply primer. After binding of the primer to the template DNA, DNA synthesis extends to the other end by DNA polymerase. PCR cycle is generally composed of the following steps:

1) Denaturation which changes double-stranded template DNA molecule into single stranded DNA molecule;
2) Annealing of the primer to the single stranded DNA template; and
3) Elongation which synthesizes a DNA molecule complementary to the template DNA by DNA polymerase.

After completion of the first PCR cycle, the original template DNA and the PCR product are both used as DNA templates in the subsequent PCR cycle. So, as PCR cycle is repeated, the number of DNA templates is increasing. In an idealized case, the number of existing DNA molecules in a PCR is 2n after n cycles. As a result, (2n−1) copies of the original template DNA are synthesized. In PCR cycles, the first step is the template denaturation step. The template denaturation step requires high temperature of at least 90° C. In this step, DNA polymerase may be denatured. The DNA polymerases initially employed have low thermo-stability which is called mesophilic DNA polymerase. In this case with mesophilic DNA polymerase, fresh DNA polymerase has to be added to the PCR reaction mixture in each PCR cycle. However, since a thermo-stable DNA polymerase was found in *Thermus aquaticus*, a thermopile living in hot spring, the addition of fresh DNA polymerase to PCR reaction mixture in each PCR cycle has not been necessary and DNA polymerase is added just once when PCR is started. The optimal temperature for this kind of thermo-stable DNA polymerase (Taq DNA polymerase) is 72° C. and it is still stable at 94° C. The discovery of the thermo-stable Taq DNA polymerase facilitated PCR and paved a way for PCR to be used in various research fields (Science 252: 1643-1651, 1991). So now, PCR is acknowledged as a powerful technique used in various research fields.

Since the discovery of the thermo-stable Taq DNA polymerase, PCR techniques have been astonishingly advanced mainly by the discovery of novel DNA polymerases and the development of novel PCR techniques. Newly discovered or developed DNA polymerases are Tth DNA polymerase (from *Thermus thermophilus*), Tfl DNA polymerase (from *Thermus flavus*), Hot Tub DNA polymerase (from *Thermus ubiquitos*), Ultma DNA polymerase (from *Thermotoga maritima*), Pfu DNA polymerase (from *Pyrococcus furiosus*), Vent DNA polymerase (from *Thermococcus litoralis*) and Tli DNA polymerase (from *Thermococcus litoralis*) and Pwo DNA polymerase (from *Pyrococcus woesei*). Because these DNA polymerases are distinguished from one another in their characteristics, they have been utilized in different PCRs according to their unique properties. Precisely, they are different in DNA synthesizing speed, the number of nucleotides synthesized from the binding of the polymerase to a template DNA to the separation, preference to the kinds of template-primer, and sensitivity to inhibitory materials. Recently, a method has been developed to use at least two of these DNA polymerases together. Using this blend of different DNA polymerases is expected to have advantages because merits of both or multiple DNA polymerases can be all utilized or the overall inhibitory effect by an inhibitor can be reduced.

PCR techniques developed so far are as follows: rapid PCR characterized by reduced time for amplification; direct PCR capable of direct using of unpurified samples; reverse transcriptase-PCR (RT-PCR) which combines reverse transcription with PCR and thereby can use RNA molecule as a template; and real-time PCR facilitating real-time monitoring of PCR reaction. In addition, many techniques and methods have been developed but detailed explanations on these are not given herein.

In parallel with the development of new DNA polymerases and novel PCR techniques, studies have been undergoing to reduce "non-specific amplification" which is very a common problem encountered in general PCR. The major cause of non-specific amplification is that some primers in PCR reaction mixture anneal to templates before reaction temperature reaches desired and proper reaction temperature for PCR and then amplification by DNA polymerase is induced already to some degree. Besides, such non-specific amplification can also be significantly induced when an inappropriate primer not capable of securing the annealing between a template and a primer is used. Instructions have been given to design an appropriate primer which is well understood by those in the art, so that explanation is not necessary herein. There are other reasons for the non-specific amplification, for example inappropriate magnesium ion concentration in PCR reaction mixture, etc, but the major causes are the above two, so that minor causes are not explained herein.

As mentioned hereinbefore, in general PCR, a target sequence of a template is amplified by repeated PCR cycle of annealing and elongation after denaturation of the template DNA. The proper reaction temperature for PCR is generally higher (at least 40° C.) than room temperature (20-35° C. in general). But, as explained hereinabove, annealing between a primer and a template can happen at room temperature which leads to the amplification by DNA polymerase. Such amplification induced before reaching proper PCR temperature is based on non-specific template-primer annealing, so that it resultingly causes serious non-specific amplification. Annealing between a primer and a template happening at a less stringent annealing temperature lower than proper PCR reaction temperature is characterized by low specificity, so that the amplification based on such annealing with low specificity might include amplification of other non-target regions as well as a target region. The annealing between a template and a primer is generally determined by Tm of the used primer, which is also well known fact to those in the art, so that the additional explanation on that is not given here in this invention.

According to the conventional art, in order to reduce non-specific amplification at room temperature, a crucial component for PCR is not added to the PCR reaction mixture during the initial set-up stages of PCR and just prior to PCR cycling the component is added lastly (Nucleic Acids Res. 19: 3749, 1991). Magnesium ion has been selected as the omitted component in this conventional method. But, the conventional method does not facilitate the preparation of PCR reaction mixture at a time, causing inconvenience for experimenters.

Another example of the conventional art is that DNA polymerase is withheld physically, chemically, or biochemically not to participate in the amplification until temperature reaches desired and proper temperature for PCR. For this method, an antibody has been used (BioTechniques 16: 1134-1137, 1994). Or a chemical that is able to inactivate DNA polymerase by chemical modification has been used (the representative example of chemically modified DNA polymerase is AmpliTaq Gold DNA polymerase). Oligo-nucleotide binding to the active site of DNA polymerase has been also used (J. Mol. Biol. 264: 268-278, 1997). DNA polymerase physically, chemically, or biochemically arrested by foregoing materials is not functional at room temperature and once temperature reaches to denaturing temperature of a template during PCR, the arrested DNA polymerase is released and begins to work normally by the effect of the high temperature. As a result, the amplification at room temperature can be suppressed and accordingly hot-start PCR can be realized. Precisely, a chemical modifier that arrests DNA polymerase is degraded at template-denaturing temperature or an antibody or oligonucleotide is taken apart from DNA polymerase, so that DNA polymerase can work normally, suggesting that amplification by PCR is carried out after the denaturation stage of a template. This method has been quite effective so far, so that it has been widely used. However, this method has disadvantages of high costs and complication for its accomplishment.

It has been requested to develop a novel technique performed with less costs and with easy. To meet the request, it has been tried that amplification is suppressed until reaction temperature reaches to the proper temperature for PCR only by manipulating a primer. An example of the above trial is described in Korean Patent No. 649165. According to this description, a regulator was additionally inserted in the original primer. This regulator is polydeoxyinosine linker and inosine that composes the regulator is a universal base which has lower Tm than general nucleotides such as G, A, T and C. Therefore, polydeoxyinosine linker forms a bubble like structure at specific temperature to inhibit non-specific binding of a primer to a template, resulting in the inhibition of non-specific amplification of PCR. Compared with the said conventional arts, this method requires less cost for the accomplishment but a unique primer containing inosine is necessary, suggesting that this method is still inconvenient. Besides, annealing temperature (proper reaction temperature for PCR) of the first PCR cycle has to be different from that of the second PCR cycle, still causing inconvenience. The use of different annealing temperatures over the PCR cycle enables the additional sequence inserted into the original primer as well as the original primer sequence to participate in annealing between a template and a primer from the second PCR cycle. These different annealing temperatures over the PCR cycle are not always necessary but for the efficient PCR, the annealing temperature has to be switched over the PCR cycles. According to the above method, pre-selective arbitrary nucleotide sequence has to be added to 5'-terminus of primer but at this time, the pre-selective arbitrary nucleotide sequence is supposed not to be complementary to any of regions of target gene sequence, which makes the method more complicated and if the entire target gene sequence is not identified the success of this method will be in doubt. So, a novel method asking lower prices with easiness is needed.

The technique to reduce non-specific amplification is of course important for PCR, particularly for PCRs utilized in gene analysis or diagnosis of a disease.

The present inventors tried to develop a novel method which is simple and requires less costs. As a result, the inventors developed a PCR primer capable of inhibiting non-specific amplification by supporting both hot-start PCR and the amplification of PCR product rather than the amplification of original template, leading to the completion of this invention.

Numbers of papers and patent descriptions have been cited in this description and the citation is marked in parentheses. The descriptions of cited papers and patent documents are attached in this invention so that the art and text of this patent can be more clearly understood.

DISCLOSURE

Technical Problem

It is an object of the present invention to overcome the problems of the conventional art and to provide a novel method requested for a long time to overcome such problems.

It is also an object of the present invention to provide a PCR primer capable of inhibiting non-specific amplification of PCR by supporting both hot-start PCR and the amplification of PCR product rather than the amplification of original template and a PCR method using the same.

Technical Solution

To achieve the above objects, the present invention provides an PCR primer which is prepared by inserting an additional reverse-complementary sequence to a certain region starting from the 5'-start site of the 5'-terminus of the original primer which is composed of priming sequence to anneal to a PCR template into the 5'-terminus of the original primer and is capable of suppressing PCR reaction before reaching desired and proper temperature for PCR and inhibiting amplification of the original template from the third PCR cycle, so as to reduce non-specific amplification and a PCR method using the same.

"Template" in this invention indicates a molecule containing target gene sequence to be amplified by PCR, and this template has to be added to PCR reaction mixture in the set-up stage of PCR. This molecule, thus, is generally DNA. "Original template" in this invention indicates the template added to PCR reaction mixture in the beginning set-up stage of PCR, which is distinguished from the PCR product which can also act as a template in the subsequent PCR cycle. That is, "Original template" indicates the template added during the initial set-up stage of PCR before PCR starts.

"Primer" in this invention indicates an oligonucleotide necessary for PCR, which is a kind of short single stranded DNA. "Original primer" in this invention indicates the common primer comprising priming sequence, which is distinguished from the primer of the present invention. In this field, the original primer might contain, in addition to the priming sequence for annealing with a template, an additional sequence such as restriction enzyme recognition sequence for the following experiment after PCR or arbitrary sequence. In this invention, "additional sequence" is a reverse-complementary sequence to a certain region of the original primer sequence composed of the sequence priming to a template, which makes the difference from the foregoing additional sequence of common primer. The primer of the present invention contains a template-specific sequence basically and then the reverse-complementary sequence to a certain region of 5'-terminus of the template-specific sequence additionally, indicating that template-specific sequence and its reverse-complementary sequence are included in the same primer, which makes the difference from the common PCR primers.

"Non-specific amplification" in this invention indicates the amplification of other non-target gene sequence than a target gene sequence. In general, it is better to reduce the non-specific amplification.

"Hot-start PCR" in this invention indicates the PCR in which amplification is not started until temperature reaches to proper reaction temperature for PCR. Precisely, PCR is suppressed at ambient temperature (normal temperature: room temperature) at which PCR reaction mixture is prepared.

"Proper reaction temperature for PCR" in this invention indicates the temperature securing specificity of primer-template annealing. In general PCR cycle, template-specific primer annealing process is necessary. For such template-specific primer annealing, a specific temperature is required, which is called "proper reaction temperature for PCR" herein. The proper reaction temperature for PCR largely depends on Tm of a primer and is commonly at least 40° C. in general PCR.

The lower temperature than the "proper reaction temperature for PCR" is called "room temperature" in this invention. Room temperature or ambient temperature indicates the outside temperature at which PCR reaction mixture is prepared and the prepared PCR reaction mixture is transferred into a PCR machine and exposed. Because the room temperature is lower than the proper reaction temperature for PCR, specificity of template-primer annealing is not guaranteed at this temperature. Therefore, amplification at room temperature is non-specific.

"Denaturing temperature" in this invention indicates the temperature at which template DNA is denatured into single stranded DNA. In general, the denaturing temperature is at least 90° C.

The present invention is described in detail hereinafter.

The primer of the present invention is distinguished from the common primer or that contains polydeoxyinosine linker in the respect of having a reverse-complementary sequence in its own sequence.

There are some descriptions regarding the primers having a complementary sequence. For example, Kaboev et al developed a method that uses the primer having molecular beacon structure for hot-start PCR (Nucleic Acids Res. 28: e94-e95, 2000). According to this method, the primer has to have a complementary sequence at both ends and the primer has to form hairpin structure by intra-molecular hybridization based on the complementary sequences at both ends. So, there is structural and functional difference between the prior primer and the primer of the present invention.

PCR reaction mixture is generally prepared at room temperature and the prepared PCR reaction mixture is transferred into a PCR machine and then PCR is induced at proper temperature that an experimenter has already set. But, in fact, amplification might start from when the PCR reaction mixture is prepared, that is before PCR reaction temperature reaches to the proper reaction temperature for PCR. This is because all PCR components are already included in the PCR reaction mixture and DNA polymerase exhibits some polymerase activity. Room temperature is actually much lower temperature not only than the proper reaction temperature for PCR but also than the optimum temperature for DNA polymerase. Therefore, DNA polymerase activity is lower at room temperature than at the optimum temperature, but the enzyme still exhibits its enzyme activity that is capable of inducing amplification. As explained hereinbefore, this amplification at less stringent annealing temperature is characterized by significantly high non-specificity, compared with the amplification at the proper reaction temperature for PCR. So, it is important to suppress amplification at room temperature.

The present inventors were able to suppress significantly the amplification at room temperature by inserting the additional reverse-complementary sequence to a certain region starting from the 5'-start site of 5'-terminus of the original primer composed of the priming sequence to anneal with a template into the 5'-terminus of the original primer. A schematic diagram illustrating the primer of the present invention is presented in FIG. 1. In FIG. 1, the complementary sequence in the primer is represented with lines to help understanding. As shown in FIG. 1, a sort of linker sequence can be additionally inserted in order to give structural flexibility between the additional reverse-complementary sequence and the original primer sequence. The linker sequence is not limited in its length and sequence but is preferably not too long. If the linker sequence is too long, the full length of the primer will be too long, which is not preferred.

PCR using the primer of the present invention shown in FIG. 1 has two advantages. First, amplification at less stringent annealing temperature such as room temperature can be inhibited. Second, amplification of the original template is minimized and instead amplification of PCR product becomes dominant, suggesting that amplification specificity can be improved.

Inhibition of amplification at room temperature is induced by the following mechanisms. The primer of the present invention added in PCR reaction mixture may exist as one of the two forms at room temperature presented in FIG. 2, and accordingly it cannot be involved in amplification at room temperature. The primer of the present invention may form a secondary structure by intra-molecular hybridization or a primer-dimer by inter-molecular hybridization; as a result it cannot take part in PCR amplification at room temperature. As shown in FIG. 2, inter-molecular hybridization favors forming more stable structure with higher number of complementary binding site than intra-molecular hybridization. So, mechanism based on primer-dimer formation seems to be persuasive. The inter- or intra-molecular hydrogen bondings in the inactivated primers are broken as shown in FIG. 2 after denaturing stage of a template, and then when PCR reaction temperature reaches to the proper reaction temperature for PCR, these primers anneal with a template, leading to template-specific amplification. The proper reaction temperature for PCR is the temperature set for supporting specific template-primer annealing, so at this stringent annealing temperature, specific template-primer annealing is dominant over intra-molecular hybridization of a primer or primer-dimer formation.

During PCR cycling, dependence on the original template becomes lower and amplification of PCR product (secondary template) becomes dominant, which is described in more detail in FIG. 3. After the first PCR cycle, the PCR reaction mixture contains two templates: the original template and the PCR product produced from the first PCR cycle. In the second PCR cycle, the original template and the PCR product produced from the first PCR cycle can act as templates. From the third PCR cycle, the primer of the present invention is favored to anneal to the PCR product rather than to the original template. This is because the PCR product generated from the second PCR cycle has more complementary binding sites with the primer of the present invention than the original template. So, since the third PCR cycle, amplification using the PCR product as a template becomes dominant, and as PCR cycle repeats, amplification of the original template is suppressed. This suggests that amplification of the original template including various non-target gene sequences as well as the target gene sequence can be suppressed, which can be a fundamental solution for reducing non-specific amplification. That is, it is expected that amplification using the PCR product as a template gives higher specificity because the PCR product has only a target gene sequence. When the primer of the present invention is used, the number of complementary binding sites between a template and a primer increases as many as the number of base composing the additional reverse-complementary sequence added to the original primer from the third PCR cycle, leading to the tight template-primer annealing, indicating the improvement of specificity of PCR. Even though the non-specifically amplified product is generated from the first PCR cycle, the amplification of the PCR product amplified specifically becomes dominant over the amplification using the non-specifically amplified product from the third PCR cycle, suggesting that specificity of PCR increases. The present invention characteristically presents a PCR method using the specifically amplified PCR product as a template rather than using the original template or the non-specifically amplified product as a template. So, the present invention can provide improved specificity of PCR.

The primer of the present invention is composed of a priming sequence to anneal with a template and an additional reverse-complementary sequence to a certain region starting from the 5'-start site of the 5'-terminus of the priming sequence and a supplement sequence such as a linker sequence between the priming sequence and the above additional reverse-complementary sequence.

The primer of the present invention favors "primer-dimer formation" rather than "intra-molecular hybridization". So, it is expected that "primer-template annealing" is stronger at the proper reaction temperature for PCR than "primer-dimer formation". So, the number of possible complementary binding sites in primer-dimer resulted from the addition of the reverse-complementary sequence is necessarily fewer than that of "primer-template annealing". The number of possible complementary binding sites in primer-dimer is double the number of bases in the additional reverse-complementary sequence, but this number has to be fewer than the number of possible complementary binding sites in "primer-template annealing". However, the fewer number of possible complementary binding sites does not always indicate weaker binding. So, regulation of GC ratio of primer is also necessary. But, the regulation of the number of possible complementary binding sites with consideration of GC ratio of primer is very complicated and not easy, so it is preferred to make the additional reverse-complementary sequence as short as possible. Not necessarily but preferably, the number of base of the additional reverse-complementary sequence is supposed to be smaller than half the number of possible complementary binding sites between primer-template (corresponding to the number of base composing the priming sequence of the original primer).

It is preferred to increase GC ratio of primer to reduce the number of base composing the additional reverse-complementary sequence with maintaining enough binding force at room temperature. In general, as GC ratio of primer goes high, binding force between primer-template becomes stronger. The reverse-complementary sequence added to the primer of the present invention has preferably 1-15 bases, more preferably 2-12 bases, and most preferably 3-8 bases.

Expecting GC ratio of primer applicable for the additional reverse-complementary sequence is 20-100% by the base of the entire primer sequence, more preferably 35-95%, most preferably 50-90%. The primer-template binding has to be stronger than intra-molecular or inter-molecular hybridization at proper reaction temperature for PCR. Therefore, when an additional reverse-complementary sequence is added, it is not preferred to try to increase GC ratio and length of the reverse-complementary sequence together. It is better to try to increase GC ratio with shorter additional sequence.

The length of the original primer is not limited in the designing and synthesis of the primer of the present invention. According to the present invention, the length of the original primer can be shortened compared to the common primer. For example, if the minimum required number of bases in primer for amplification of target sequence is 18, the length of the primer of the present invention can be reduced to 13 for obtaining same amplification efficiency. This is realized because template-primer annealing specificity is improved by the method of the present invention. If a length of a primer is too long, primer-dimer is formed or non-specific binding between primer-template is induced at proper reaction temperature for PCR. So, the length of a primer is preferably regulated. The length of a primer is preferably 10-50 nucleotides, more preferably 10-40 nucleotides, and most preferably 10-35 nucleotides.

In a preferred embodiment of the present invention, an additional reverse-complementary sequence is added to both forward primer and reverse primer according to the method of the present invention. However, it is not a problem to add such an additional reverse-complementary sequence to one of the primers, although adding to both primers is preferred.

In a preferred embodiment of the present invention, PCR using Taq DNA polymerase is described, but the PCR method of the present invention can be applied to any PCR using any DNA polymerase, without limitation. The DNA polymerase herein is exemplified by Taq DNA polymerase, Tth DNA polymerase, Tfl DNA polymerase, Hot Tub DNA polymerase, Ultma DNA polymerase, Pfu DNA polymerase, Vent DNA polymerase, Tli DNA polymerase and Pwo DNA polymerase (all brand names), but not always limited thereto.

The method of the present invention can be applied in any RT-PCR as well as in any PCR. The application in RT-PCR is well understood by those in the art, so that the explanation about the application in RT-PCR is not repeated herein.

Advantageous Effect

According to the method of the present invention, non-specific amplification can be reduced simply by regulating the sequence of a PCR primer, resulting in PCR with less cost but improved specificity. The present invention can be applied in any PCR but can be more efficiently used for PCRs utilized in gene analysis, disease diagnosis, and the development of a diagnostic product. The primer prepared according to the method of the present invention can be also used in the conventional and commercial PCR-related product for hot-start PCR and in this case, it brings improved specificity.

DESCRIPTION OF DRAWINGS

The application of the preferred embodiments of the present invention is best understood with reference to the accompanying drawings, wherein:

FIG. 1 also shows possible primer-template annealing, but it is just for helping to understand the structure of the primer and does not suggest that the binding shown in FIG. 1 forms as it is shown. (A) no-linker sequence inserted, (B) linker sequence inserted.

FIG. 3 is a schematic diagram illustrating that the amplification of PCR product becomes dominant from the third PCR cycle over the amplification of the original template. FIG. 3E shows the original template and second PCR product prior to the third PCR cycle.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Inhibition of Non-Specific Amplification

Non-specific amplification inhibitory effect of the method of the present invention was investigated as follows. An original forward primer having the sequence of 5'-CCTAT-CAACTTTCGATGGTAGT-3'(22-mer, SEQ. ID. NO: 1) and an original reverse primer having the sequence of 5'-CGCTCCACCAACTAAGAACG-3'(20-mer, SEQ. ID. NO: 2) were prepared. And primers having an additional reverse-complementary sequence were prepared. The prepared forward primer had the sequence of 5'-GATAGGC-CTATCAACTTTCGATGGTAGT-3'(28-mer, SEQ. ID. NO: 3) and the prepared reverse primer had the sequence of 5'-GGAGCGCGCTCCACCAACTAAGAACG-3'(26-mer, SEQ. ID. NO: 4). The underlined parts in the above sequences were the additional sequences added for complementary binding with 5'-terminus of the original primer. In this example, the original primer not added with an additional sequence and the primer prepared by the method of the present invention which characteristically contained an additional reverse-complementary sequence were both prepared to examine the effect of the present invention.

The basic composition of the PCR reaction mixture in this example was as follows: 35 mM Tris-HCl (pH 10.0), 12.5 mM $(NH_4)_2SO_4$, 12.5 mM KCl, 3.5 mM $MgCl_2$, 0.1% tween 20, 0.25% PEG 8,000, 0.1 mg/ml BSA. The prepared PCR reaction mixture was filtered by 0.2 μm filter before use.

As DNA polymerase, i-Taq™ DNA polymerase (iNtRON Biotechnology) was used according to the manufacturer's instruction.

The template used for PCR herein was GDNA (genomic DNA) extracted from the human cell line K562. The extraction of GDNA was performed using a G-Spin™ Genomic DNA Extraction kit (for Cell/Tissue) according to the manufacturer's instruction (iNtRON Biotechnology). The target gene in this example was 1 kbp sized 18S ribosomal RNA fragment. NCBI accession number of the 18S ribosomal RNA fragment is X03205.

Figure 1A:
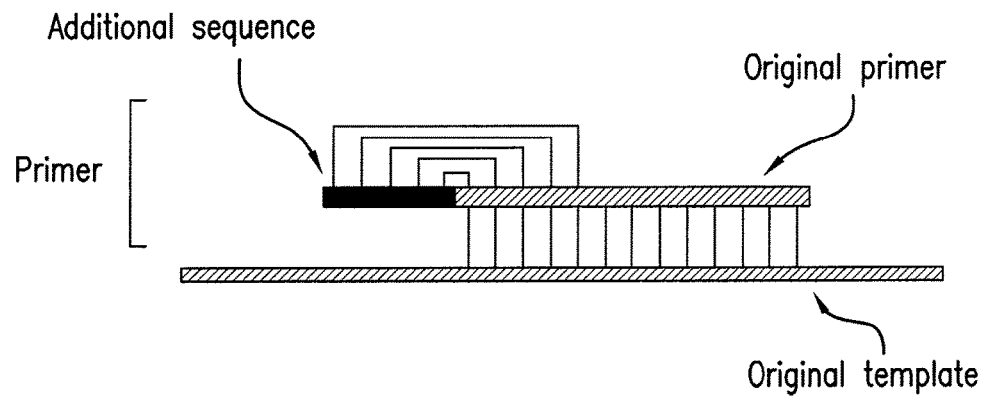
FIG. 1 is a schematic diagram illustrating the primer of the present invention designed and synthesized according to the method of the invention, which is composed of a priming sequence to anneal with a template and an additional reverse-complementary sequence to a certain region starting from the 5'-start site of the 5'-terminus of the original primer sequence that is inserted into the 5'-terminus of the original primer. A linker sequence can be additionally inserted in between the above two sequences.
Figure 1B:
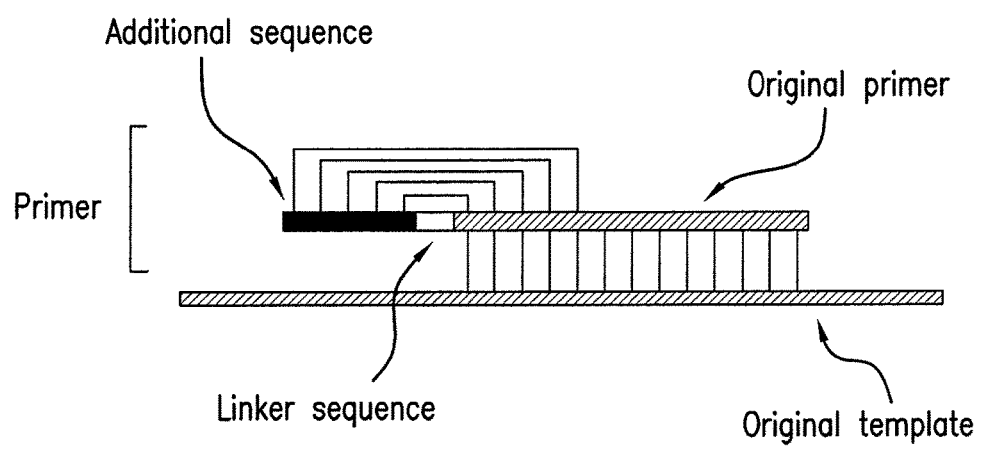
Figure 2:
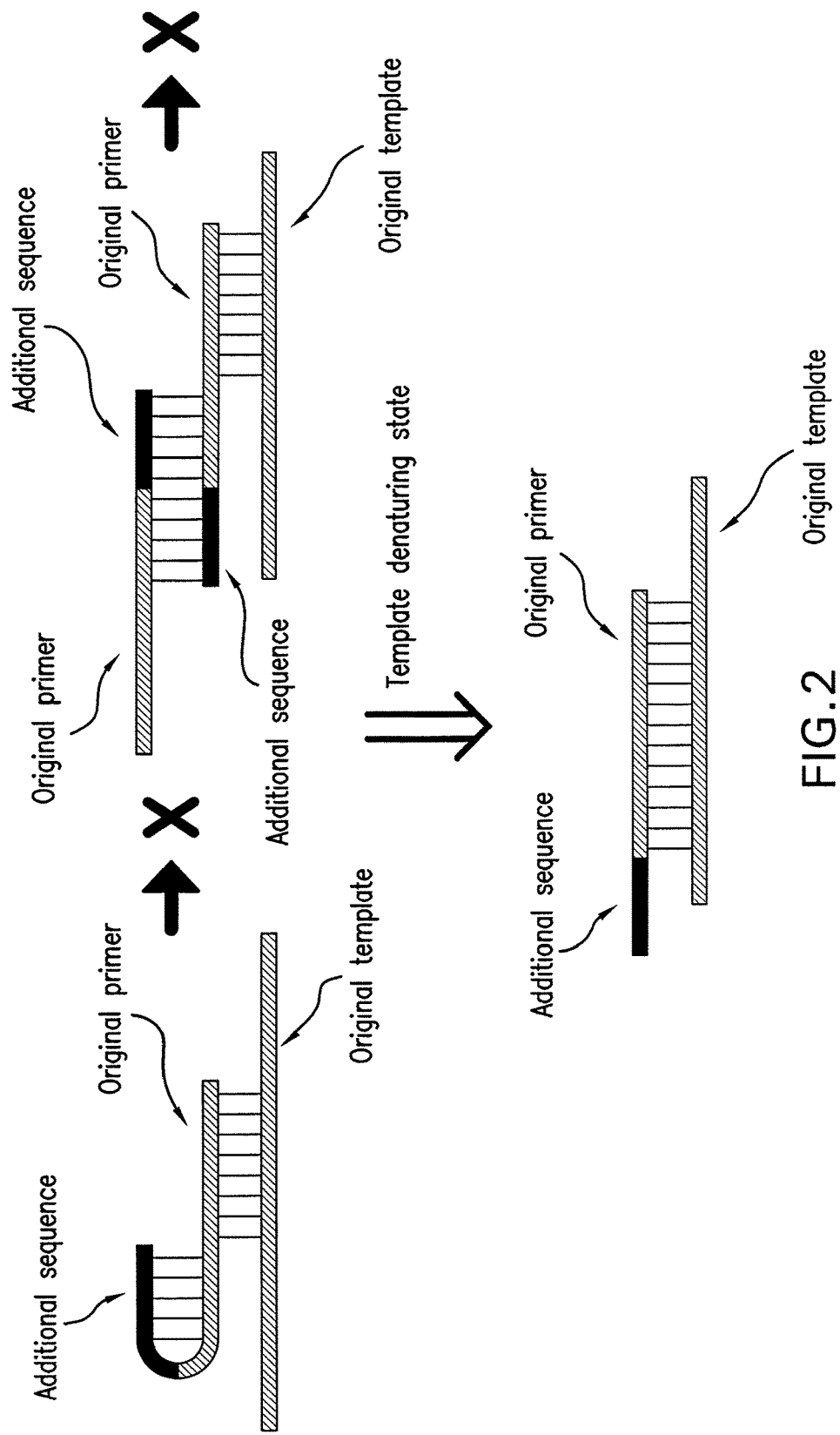
FIG. 2 is a schematic diagram illustrating the possible complementary binding in primer or between primers of the present invention at room temperature. It also shows preferable complementary binding between a primer and a template at the "proper reaction temperature for PCR" after "denaturing stage of a template".
Figure 3A:
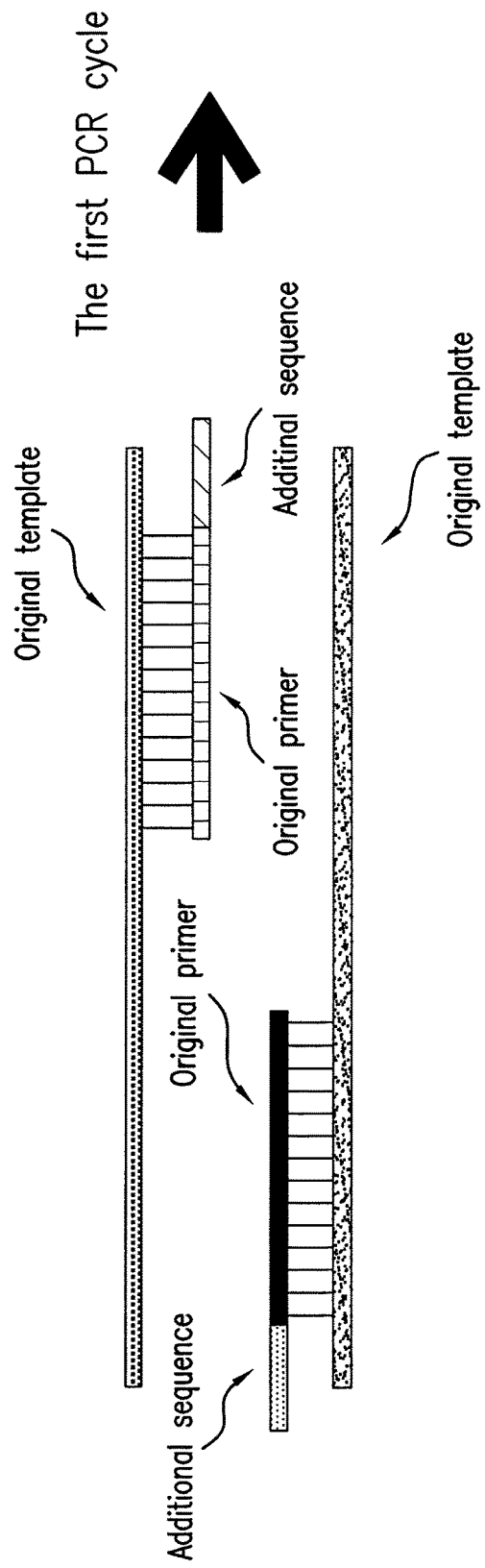
FIG. 3A shows the original template and original primers prior to the first PCR cycle.
Figure 3B:
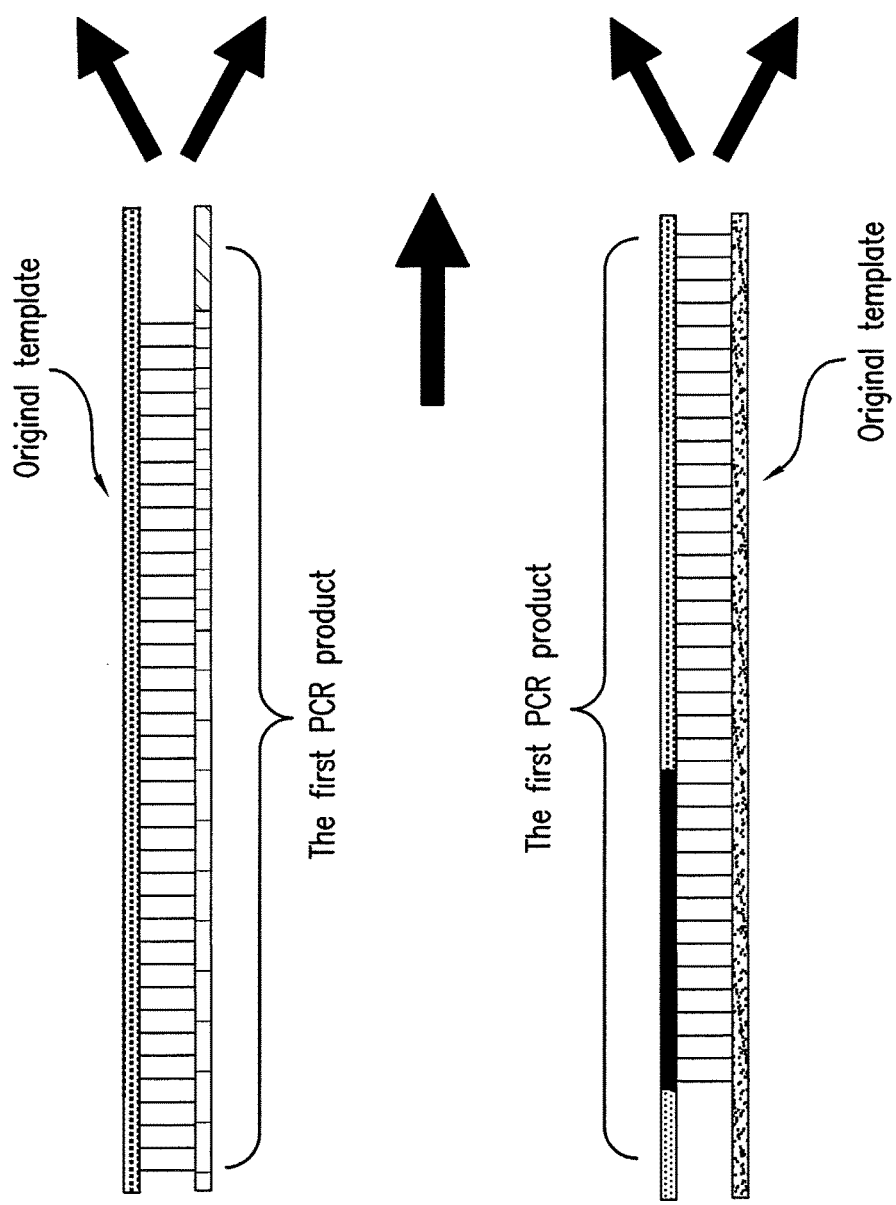
FIG. 3B shows the resulting products.
Figure 3C:
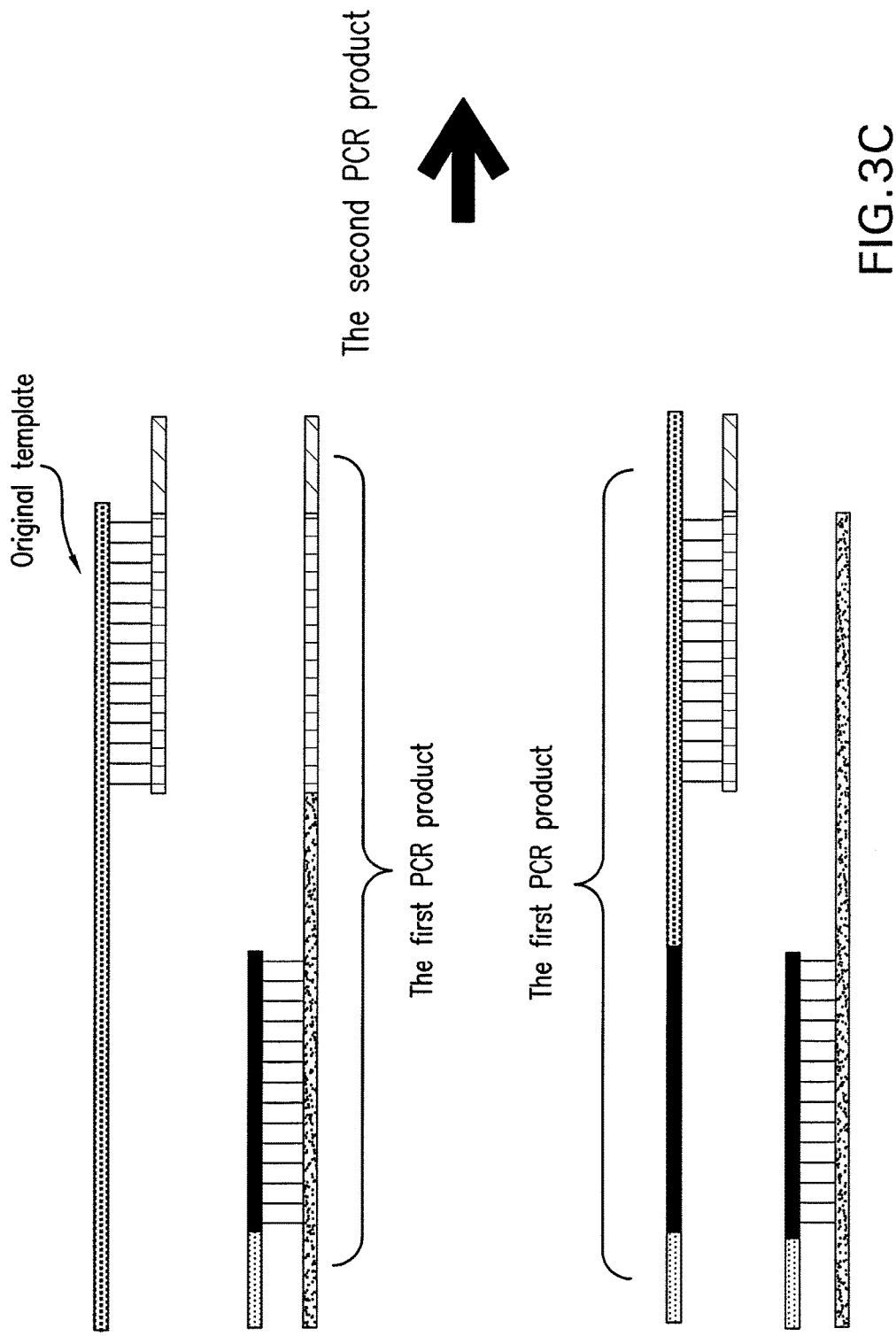
FIG. 3C shows the original template and first PCR product prior to the second PCR cycle.
Figure 3D:
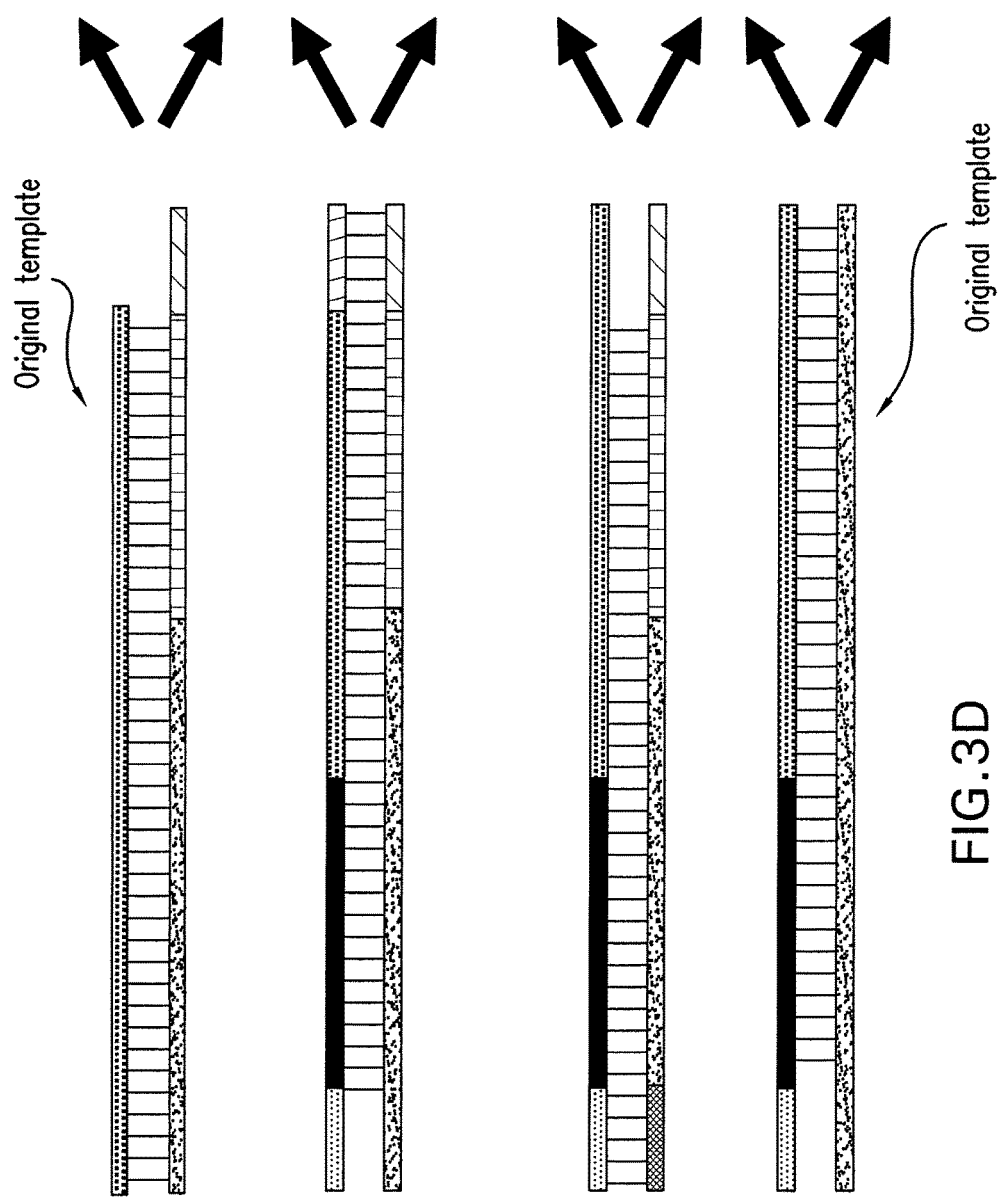
FIG. 3D shows the resulting products.
Figure 3F:
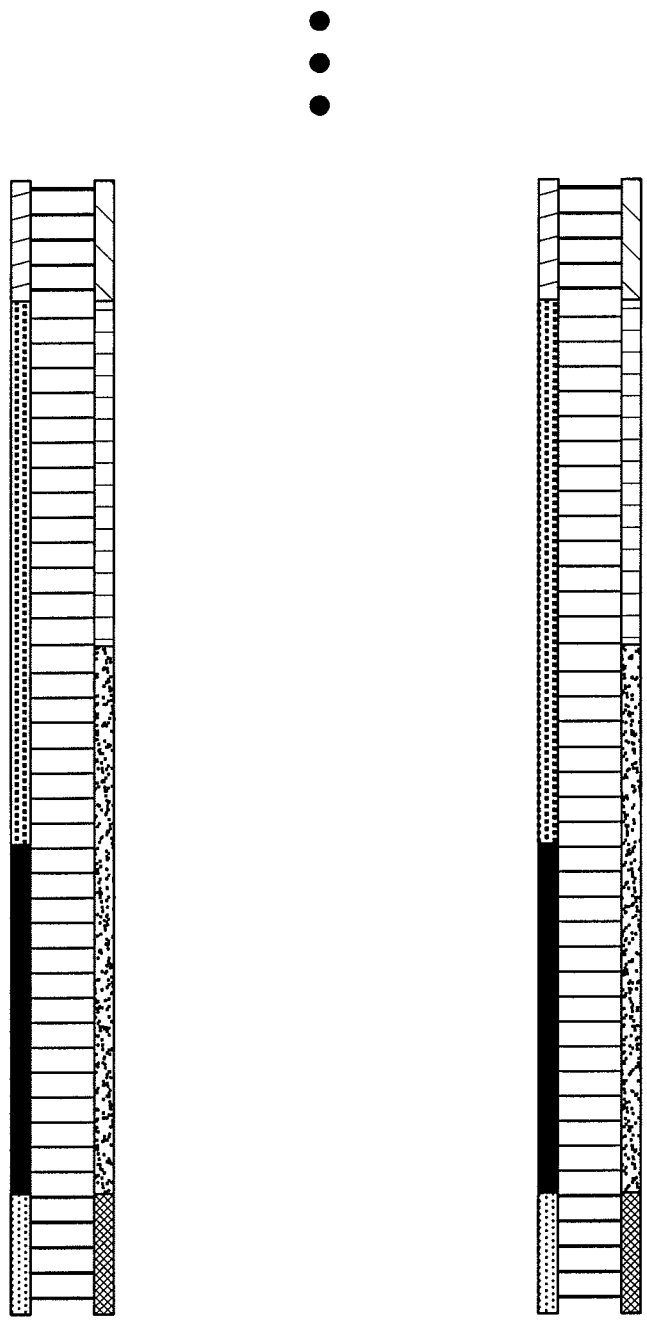
FIGS. 3F and 3G show that after the third PCR cycle, amplification using the PCR product as a template becomes dominant, and that as the PCR cycle repeats, the amplification of the original template is suppressed.
Figure 3G:
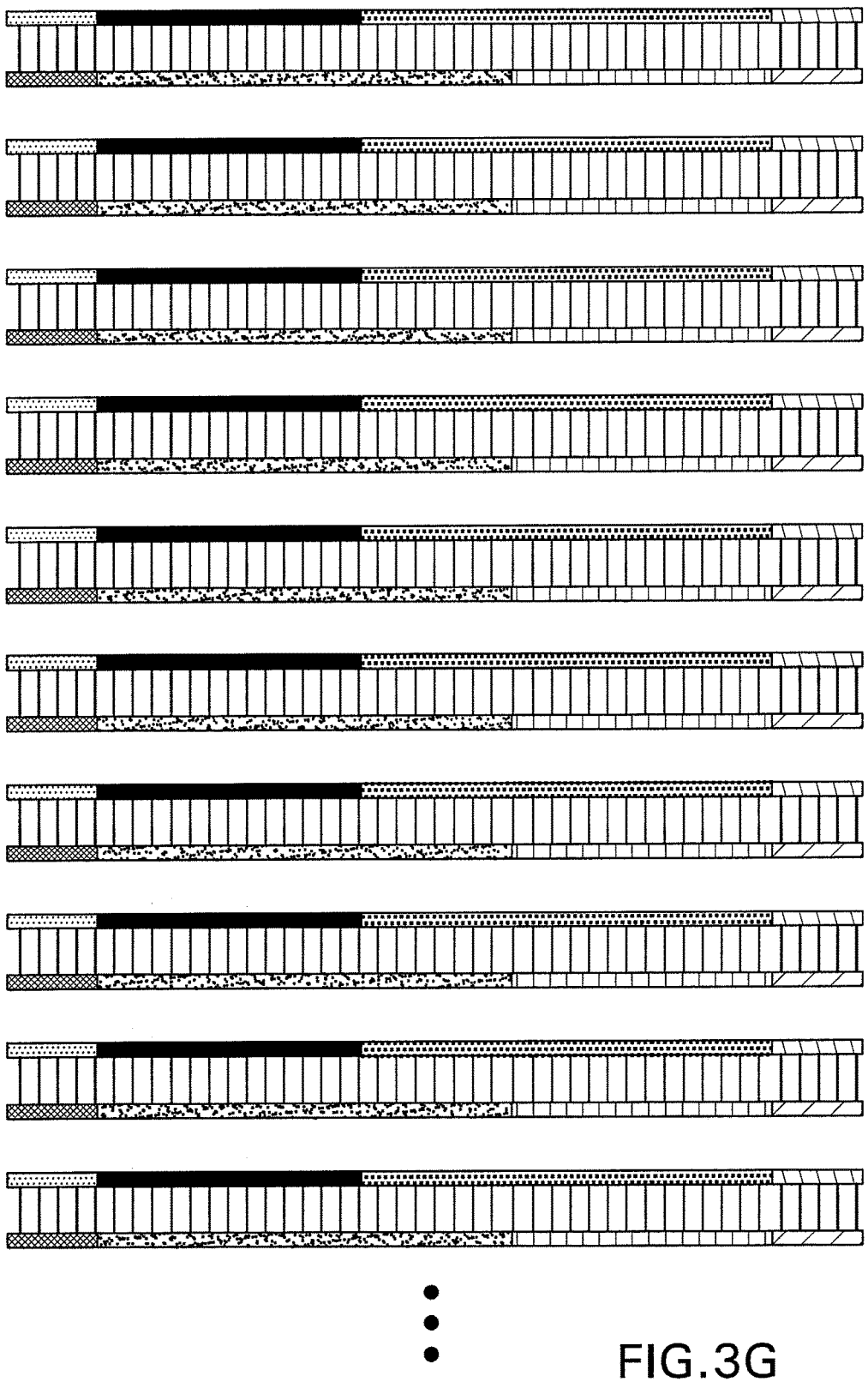
Figure 4:
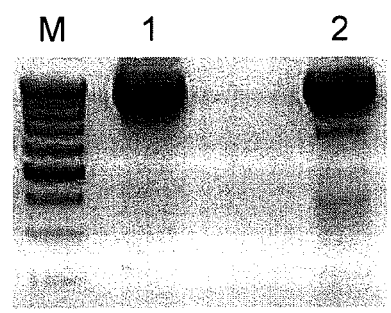
FIG. 4 illustrates the effect of the primer of the present invention on inhibition of non-specific amplification. PCR was performed respectively with the common primer and the primer of the present invention. Each PCR product was analyzed by electrophoresis on agarose gel. Lane M indicates 1 kbp sized marker; lane 1 indicates the PCR product amplified by using the primer of the present invention; and lane 2 indicates the PCR product amplified by using the common primer not following the method of the invention.

10 ng of the template DNA was added to each PCR reaction mixture prepared above. Then, each primer was added thereto at the final concentration of 10 pM. The prepared PCR reaction mixture was transferred into a PCR machine (thermal cycler), followed by PCR. PCR was performed as follows: predenaturation at 94° C. for 5 minutes, denaturation at 94° C. for 30 seconds, annealing at 52° C. (proper reaction temperature for PCR in this invention which varies from the type of primer) for 30 seconds, polymerization at 72° C. for 40 seconds, 40 cycles from denaturation to polymerization, and final extension at 72° C. for 5 minutes. Finally, the PCR product was stood at 4° C. After completion of PCR, the PCR product was analyzed by 1% agarose gel electrophoresis. The results are shown in FIG. 4. As shown in FIG. 4, approximately 1 kbp sized PCR product was identified. It was also confirmed that when the primer of the present invention was used, non-specific amplification was significantly reduced, compared with when the common primer (the original primer without an additional reverse-complementary sequence) was used. The significant decrease of non-specific amplification indicates the increase of PCR specificity, suggesting that amplification of a target gene becomes dominant.

Example 2: Effect of the Length of a Primer

The effect of the length of a primer was investigated, for which primers were designed and prepared with different lengths. In this example, the original primer was prepared to be shorter than that of example 1. The original forward primer of this example had the sequence of 5'-CCTAT-CAACTTTCGAT-3'(16-mer, SEQ. ID. NO: 5) and the original reverse primer had the sequence of 5'-CGCTCCAC-CAACTAAG-3'(16-mer, SEQ. ID. NO: 6). The primers having an additional reverse-complementary sequence were also prepared according to the method of the present invention. The prepared forward primer in this example had the sequence of 5'-GATAGGCCTATCAACTTTCGAT-3'(SEQ. ID. NO: 7) and the prepared reverse primer had the sequence of 5'-GGAGCGCGCTCCACCAACTAAG-3'(SEQ. ID. NO: 8). The underlined parts in the above sequences are the additional reverse-complementary sequences. In this example, both the primer of the present invention and the common original primer not containing such additional sequence were prepared to investigate the effect of the present invention.

The PCR reaction mixture herein had the same basic composition as shown in Example 1. The prepared PCR reaction mixture was filtered by 0.2 μm filter by the same manner as described in Example 1 before use.

The same DNA polymerase as the one used in Example 1 was used, which was i-Taq™ DNA polymerase (iNtRON Biotechnology).

The same template as the one used in Example 1 was used and the extraction method or the concentration was also consistent with that in Example 1. The target gene amplified by PCR was 1 kbp in size, which was also consistent with that of Example 1.

Figure 5:
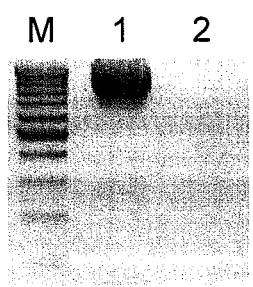
FIG. 5 illustrates the effect of the primer over the length. Precisely, PCR was performed respectively with the common primer not following the method of the present invention and the primer of the present invention. Each PCR product was analyzed by electrophoresis on agarose gel. Lane M indicates 1 kbp sized marker; lane 1 indicates the PCR product amplified by using the primer of the present invention; and lane 2 indicates the PCR product amplified by using the common primer not following the method of the present invention.

The template DNA was added to the PCR reaction mixture and then the primer was also added. When the PCR reaction mixture was ready, the mixture was transferred into a PCR machine (thermal cycler) followed by PCR by the same manner as described in Example 1. PCR conditions were also same to those in Example 1. Upon completion of PCR, electrophoresis was performed on 1% agarose gel to analyze PCR product. And the results are shown in FIG. 5. As shown in FIG. 5, when the primer prepared according to the method of the present invention was used, approximately 1 kbp sized PCR product was produced, while when the common primer (the original primer without an additional reverse-complementary sequence) was used, amplification was not induced. The above result indicates that the primer that is shorter than usual can also efficiently induce amplification.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method comprising amplifying via a polymerase chain reaction a selected target sequence with a primer, wherein the primer comprises a priming sequence and an additional sequence, wherein the priming sequence is complementary to 10-50 nucleotides of the 3' end of the selected target sequence and the additional sequence is directly attached to the 5'-terminal end of the priming sequence and is reverse-complementary to 3-15 nucleotides of the 5'-terminal sequence of the priming sequence and does not hybridize to the selected target sequence.

2. A method for reducing non-specific amplification in PCR comprising amplifying a selected target sequence via a polymerase chain reaction with a primer prepared by steps a)-c):

a) determining a priming sequence of the primer based on the selected target sequence, wherein the priming sequence is complementary to 10-50 nucleotides of the 3' end of the selected target sequence;

b) determining an additional sequence to be directly attached to the 5'-terminal end of the priming sequence of the primer, wherein the additional sequence is reverse-complementary to 3-15 nucleotides of the 5'-terminal sequence of the priming sequence and does not hybridize to the selected target sequence; and c) synthesizing the primer comprising the priming sequence and the additional sequence, wherein the additional sequence is directly attached to the 5'-terminal end of the priming sequence.

* * * * *